US006365570B1

(12) United States Patent
Van Kessel et al.

(10) Patent No.: US 6,365,570 B1
(45) Date of Patent: Apr. 2, 2002

(54) PHARMACEUTICAL AND DIAGNOSTIC USE OF SERUM AMYLOID P COMPONENT

(75) Inventors: Cornelis Petrus Maria Van Kessel, Bunnik; Johannes Antonius Gerardus Van Strijp, Schoonhoven, both of (NL)

(73) Assignee: Universiteit Utrecht (NL)

( * ) Notice: Subject to any disclaimer, the term of this patent is extended or adjusted under 35 U.S.C. 154(b) by 0 days.

(21) Appl. No.: 09/284,219

(22) PCT Filed: Oct. 10, 1997

(86) PCT No.: PCT/NL97/00567

§ 371 Date: Jun. 18, 1999

§ 102(e) Date: Jun. 18, 1999

(87) PCT Pub. No.: WO98/16556

PCT Pub. Date: Apr. 23, 1998

(51) Int. Cl.[7] .......................... A61K 38/16; A61K 38/00; A61K 35/14; C07K 14/00

(52) U.S. Cl. ................. 514/8; 514/14; 514/16; 514/17; 530/300; 530/327; 530/328; 530/329; 530/380

(58) Field of Search ................. 530/300, 380, 530/327, 328, 329; 514/8, 14, 16, 17

(56) References Cited

FOREIGN PATENT DOCUMENTS

| WO | WO-93/10800 A | * | 6/1993 | .......... A61K/35/16 |
|----|---------------|---|--------|----------------------|
| WO | WO-95/05394 A1 | * | 2/1995 | .......... C07K/14/47 |
| WO | WO-97/26906 A1 | * | 7/1997 | .......... A61K/38/17 |
| WO | WO-98/16556 A1 | * | 4/1998 | .......... C07K/14/47 |

OTHER PUBLICATIONS

Stevens et al. "In vivo inhibition of endotoxin–induced murine serum amyloid P SAP by human anti–core endotoxin J5 monoclonal IGM MAB" ABSTR Ann. meet.ing Am. Soc. of Microbiol. 89 (0), 1989.*

Emsley et al., "Structure of pentameric human serum amyloid P component", Nature, vol. 367, pp. 338–345, Jan. 27, 1994.*

Todd et al. "The acute phase protein response in mice does not show tolerance to recurrent sterile inflammation", Clinica Chimica Acta, vol. 189, pp. 47–54, 1990.*

Sipe et. al. "The role of interleukin 1 in acute phase serum amyloid A (SAA) and serum amyloid P (SAP) biosynthesis", Annales New York Academy of Sciences, vol. 389, pp. 137–150, 1982.*

Swanson et al. "Human serum amyloid P component (SAP) selectively binds to immobilized or bound forms of C–reactive protein (CRP)", Biochimica et Biophysica Acta, vol. 1160 (3), pp. 309–316, Dec. 28, 1992.*

Dyck et al. "Amyloid P component in human glomerular basement membrane", The Lancet, vol. 2, pp. 606–609, Sep. 1980.*

Wood et al. "A pentameric form of human serum amyloid P component (SAP)", J. of Mol. Biol., vol. 202(1), pp. 169–173, Jul. 1992.*

* cited by examiner

Primary Examiner—Karen Cochrane Carlson
Assistant Examiner—Rita Mitra
(74) Attorney, Agent, or Firm—Webb Ziesenheim Logsdon Orkin & Hanson, P.C.

(57) ABSTRACT

The invention relates to the new use of Serum Amyloid P component (SAP) and/or endotoxin-binding fragments thereof for the preparation of a pharmaceutical composition for neutralizing lipopolysaccharide and particularly for the treatment of sepsis. The invention further relates to a diagnostic method for demonstrating the presence of endotoxin in blood or blood fractions, such as serum or plasma.

6 Claims, 4 Drawing Sheets

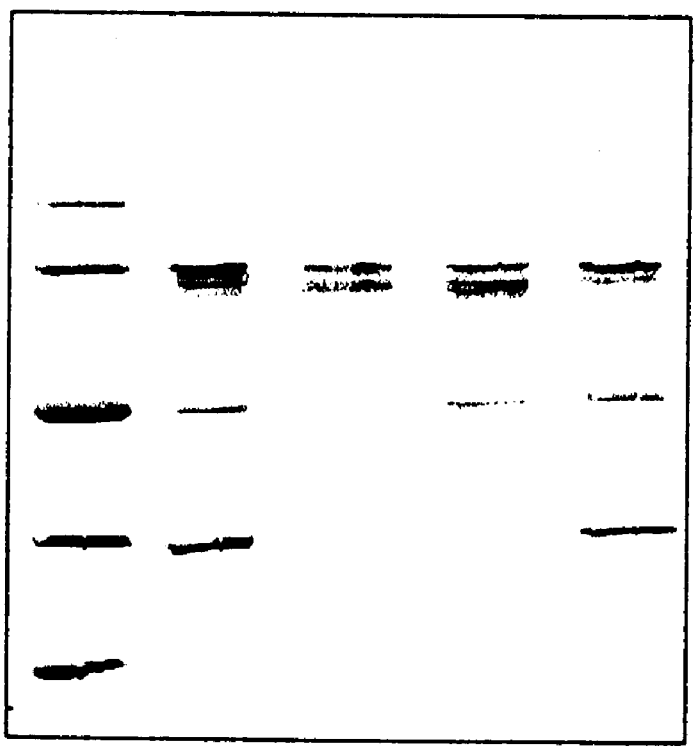 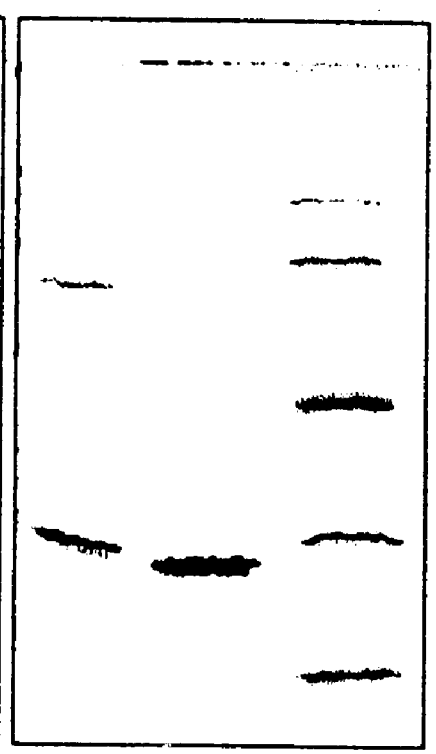

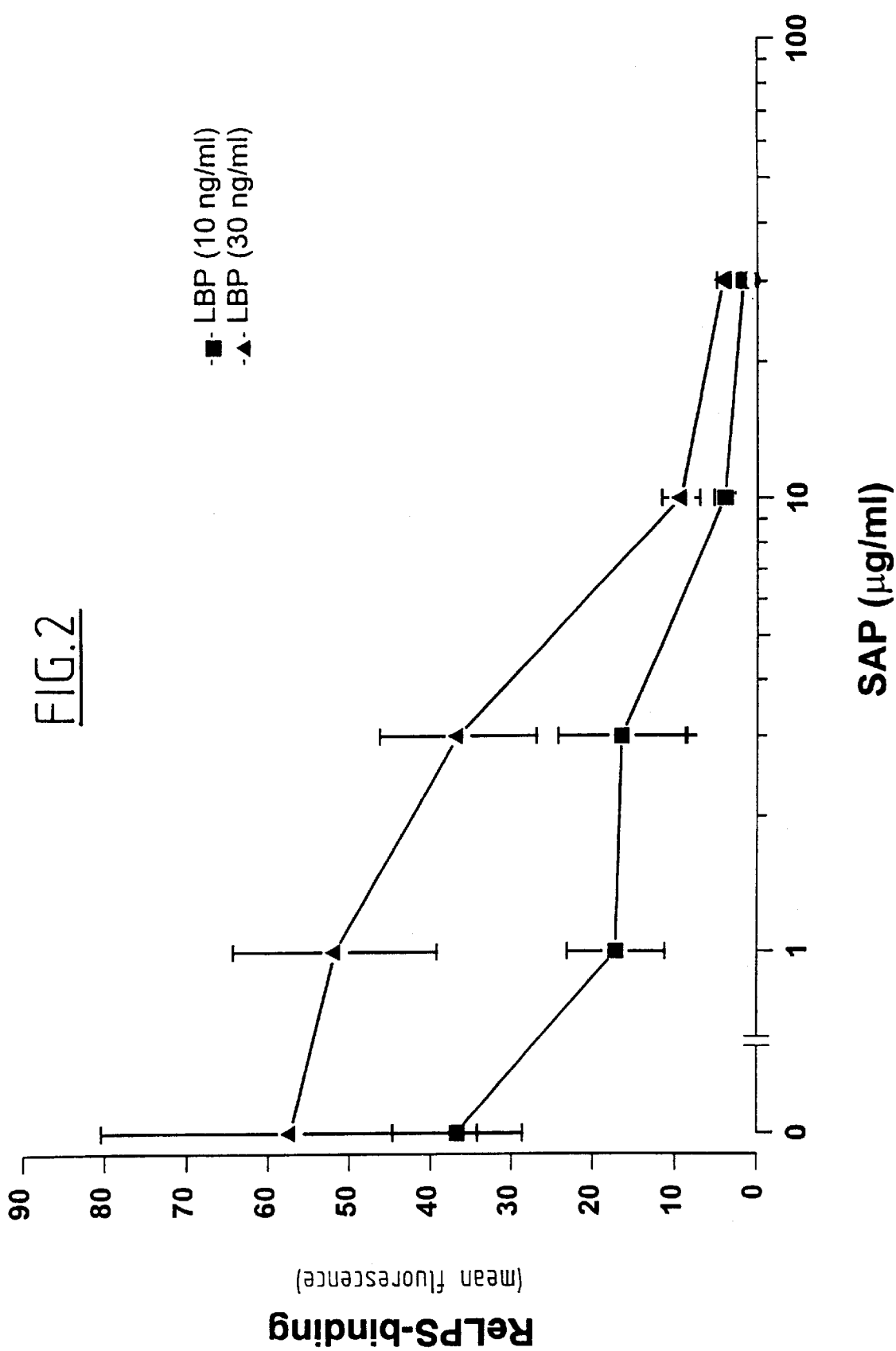

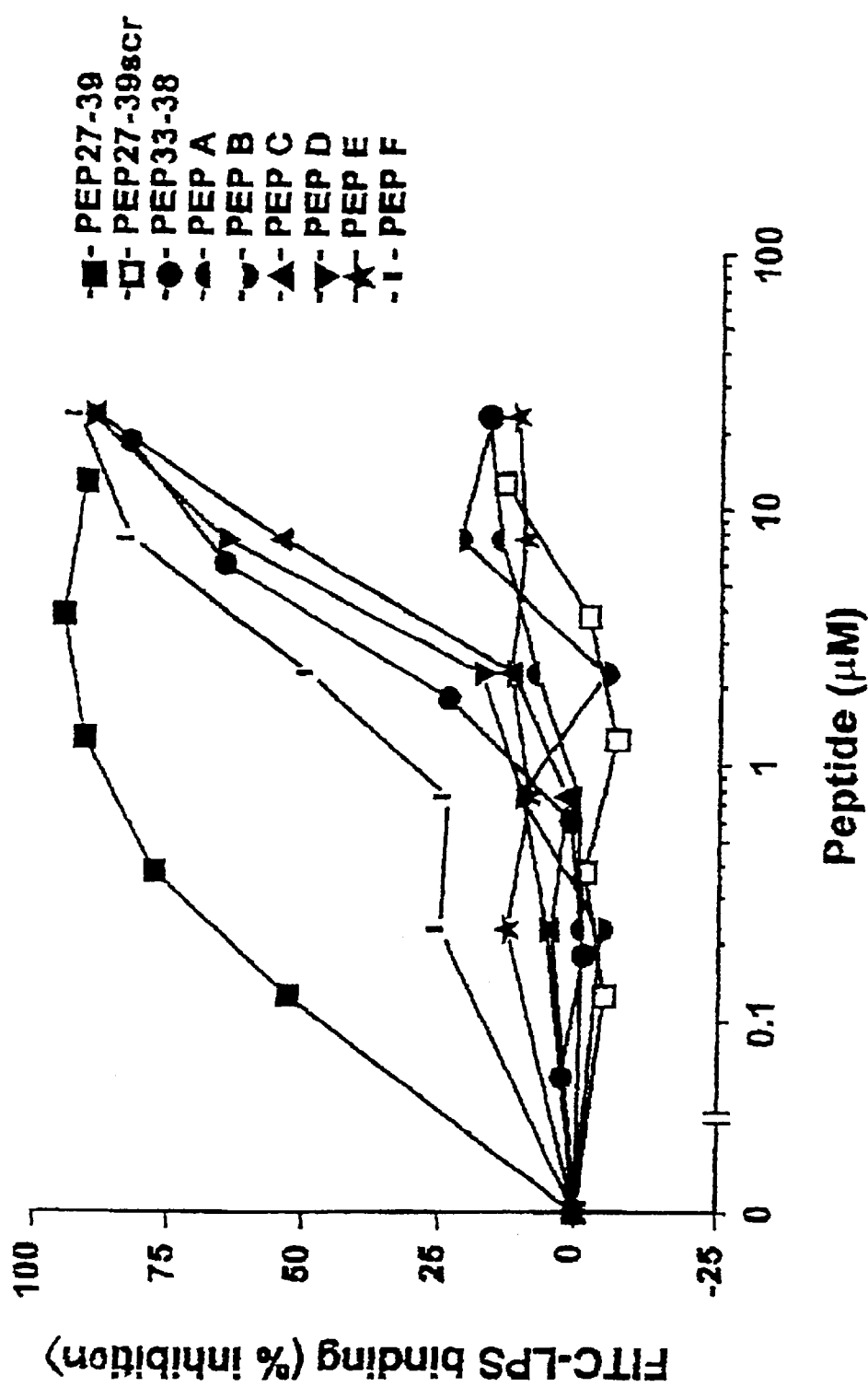

SEQUENCE LISTING

```
<160> NUMBER OF SEQ ID NOS: 8

<210> SEQ ID NO 1
<211> LENGTH: 13
<212> TYPE: PRT
<213> ORGANISM: Homo sapiens
<220> FEATURE:
<223> OTHER INFORMATION: Fragment of the Serum Amyloid P component,
      peptides 27-39

<400> SEQUENCE: 1

Glu Lys Pro Leu Gln Asn Phe Thr Leu Cys Phe Arg Ala
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Fragment of the Serum Amyloid P component,
      peptides 33-38

<400> SEQUENCE: 2

Phe Thr Leu Cys Phe Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Fragment of the Serum Amyloid P component,
      peptides 32-39

<400> SEQUENCE: 3

Asn Phe Thr Leu Cys Phe Arg Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Fragment of the Serum Amyloid P component,
      peptide 30-37

<400> SEQUENCE: 4

Leu Gln Asn Phe Thr Leu Cys Phe
1               5

<210> SEQ ID NO 5
<211> LENGTH: 8
<212> TYPE: PRT
```

```
<213> ORGANISM: Artificial Sequence
<220> FEATURE:
<223> OTHER INFORMATION: Fragment of the Serum Amyloid P component,
      peptide 29-36

<400> SEQUENCE: 5

Pro Leu Gln Asn Phe Thr Leu Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Fragment of the Serum Amyloid P component,
      peptide 31-38

<400> SEQUENCE: 6

Gln Asn Phe Thr Leu Cys Phe Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Fragment of the Serum Amyloid P component,
      peptide 28-35

<400> SEQUENCE: 7

Lys Pro Leu Gln Asn Phe Thr Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Fragment of the Serum Amyloid P component,
      peptide 27-34

<400> SEQUENCE: 8

Glu Lys Pro Leu Gln Asn Phe Thr
1               5
```

PHARMACEUTICAL AND DIAGNOSTIC USE OF SERUM AMYLOID P COMPONENT

Figure 3:
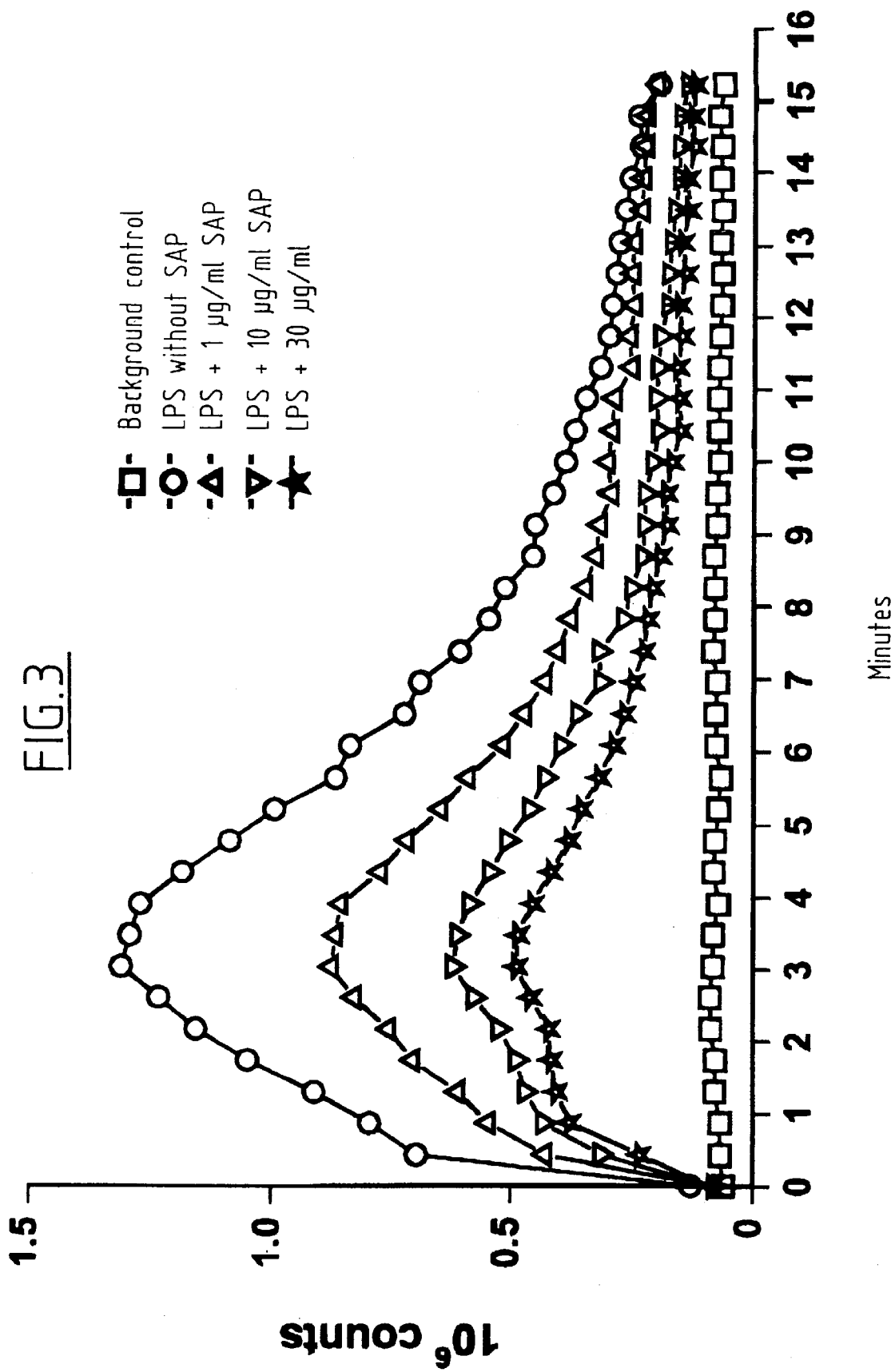

This application is a 371 of PCT/NL97/00567 filed on Oct. 10, 1997.

The present invention relates to a new method of treating sepsis. The invention further provides possibilities for therapeutic and preventive treatment of Alzheimer's disease.

Sepsis very generally comprises the clinical pictures which result from the presence of bacteria multiplying in blood. The direct cause of the symptoms are toxic substances which are released by the bacteria or released during lysis thereof. Gram-negative bacteria for instance produce lipopolysaccharides (LPS) as a component of their cell wall. These lipopolysaccharides are toxic in many circumstances. In principle they are bound to the cell and are only released when the cell lyses. Lipopolysaccharides are also referred to as endotoxins.

Infection with Gram-negative bacteria can result in a life-threatening disease which is initiated by specific binding of LPS to phagocytes, such as monocytes, macrophages and granulocytes (neutrophils). These are hereby activated and secrete various cytokines, such as tumor necrose factor-α (TNF-α), interleukin 1 (IL-1), IL-6, IL-8, and other inflammation mediators. These compounds initiate a cascade of events, either directly or by activation of secondary mediators, which ultimately result in fever and disorders in the coagulation of the blood, vasodilation, organ failure and finally septic shock.

Different treatments for sepsis have already been proposed. Thus, for the treatment of specific Gram-negative sepsis, monoclonal antibodies are for instance used against endotoxin. Tests are currently also being carried out with recombinant BPI, a product of the neutrophils with a strong lipopolysaccharide-neutralizing effect.

Used for treatment of general sepsis are antibodies aimed against cytokines or antagonists for the soluble TNF (tumor necrose factor) receptor or for the interleukin-1 receptor.

Up to the present a totally satisfactory result has not yet been achieved with the known methods.

It is therefore the first object of the present invention to provide a new method of treatment and diagnosis of sepsis.

Surprisingly, it has been found that the per se known protein Serum Amyloid P component (SAP) is capable of binding to endotoxin. Binding of the circulating SAP to the phagocytes, and therewith activation thereof, is hereby prevented. In this manner SAP is capable of neutralizing the biological action of endotoxin.

The present invention therefore relates in a first aspect to the use of Serum Amyloid P component (SAP) for the preparation of a pharmaceutical composition for neutralizing lipopolysaccharide(s) in general and the treatment of sepsis in particular.

SAP is a member of the family of the pentraxins. Pentraxins are proteins with a characteristic pentameric organization of identical subunits which are ordered as single or double annular discs. Another member of this family is the C-reactive protein (CRP). CRP and SAP are both so-called "acute-phase reactants" (APR), i.e. they are involved in the early phase of an inflammation process. Per species however, it is generally found that only one of the two acts as APR. For humans it is the case that the concentration of SAP in normal human plasma is approximately 30 μg/ml. During inflammation reactions this level remains roughly the same, while the CRP level may well be increased a thousand-fold to 1 mg/ml, depending on the disease and the seriousness thereof.

It may be considered particularly surprising that a compound which plays no part as APR during inflammation reactions is in fact capable of neutralizing sepsis-causing endotoxin. It could be expected that the body itself would make use of this neutralizing capacity by increasing the plasma level of this compound in the case of infection with Gram-negative bacteria and the inflammation reactions resulting therefrom.

SAP is a relatively large protein. For particular ligands is known which of the amino acids of SAP are involved in binding, such as for instance for CRP, C4-binding protein (C4bp), C1q and Calcium ions. It has thus also been established for endotoxin that determined regions of the SAP molecule are involved in the binding. It may therefore be recommended to use only the specific binding parts of the protein for manufacture of a pharmaceutical preparation.

According to the invention it has now further been found that SAP fragments, which consist of at least a part of the amino acids 27–39 of SAP in the sequence occurring in SAP, are very successful in inhibiting the binding of LPS to monocytes.

According to a second aspect of the invention new peptides (SAP fragments) are therefore provided for use in neutralizing lipopolysaccharides, which peptides consist of a part of the amino acids 27–39 of SAP in the sequence occurring in SAP. Preferred peptides are the PEP 27–39, which consists of the amino acids 27–39, PEP 33–38 (amino acids 33–38), PEP 32–39 (amino acids 32–39), PEP 30–37 (amino acids 30–37) and PEP 29–36 (amino acids 29–36). Table 1 below shows the amino acid composition of the different peptides.

TABLE 1

| Amino Acid Number | 27 | 28 | 29 | 30 | 31 | 32 | 33 | 34 | 35 | 36 | 37 | 38 | 39 | SEQ ID NO |
|---|---|---|---|---|---|---|---|---|---|---|---|---|---|---|
| SAP | | | | | | | | | | | | | | |
| PEP 29–39 | Glu | Lys | Pro | Leu | Gln | Asn | Phe | Thr | Leu | Cys | Phe | Arg | Ala | 1 |
| PEP 33–38 | | | | | | | Phe | Thr | Leu | Cys | Phe | Arg | | 2 |
| PEP 32–39 | | | | | | Asn | Phe | Thr | Leu | Cys | Phe | Arg | Ala | 3 |
| PEP 33–38 | | | | | Gln | Asn | Phe | Thr | Leu | Cys | Phe | Arg | | 6 |
| PEP 30–37 | | | | Leu | Gln | Asn | Phe | Thr | Leu | Cys | Phe | | | 4 |
| PEP 29–36 | | | Pro | Leu | Gln | Asn | Phe | Thr | Leu | Cys | | | | 5 |

TABLE 1-continued

| Amino Acid Number | 27 | 28 | 29 | 30 | 31 | 32 | 33 | 34 | 35 | 36 | 37 | 38 | 39 | SEQ ID NO |
|---|---|---|---|---|---|---|---|---|---|---|---|---|---|---|
| PEP 28–35 |  | Lys | Pro | Leu | Gln | Asn | Phe | Thr | Leu |  |  |  |  | 7 |
| PEP 27–34 | Glu | Lys | Pro | Leu | Gln | Asn | Phe | Thr |  |  |  |  |  | 8 |

Glu-Glutamate;
Lys-Lysine;
Pro-Proline;
Leu-Leucine;
Gln-Glutamine;
Asn-Asparagine;
Phe-Phenylalanine;
Thr-Threonine;
Cys-Cysteine;
Arg-Arginine;
Ala-Alanine The advantage of SAP fragments is that they can be manufactured more simply owing to their smaller dimensions and can penetrate more easily into bodily tissues.

In the research which led to the present invention it was further inferred that LPS is possibly involved as environmental factor in the development of Alzheimer's disease. Alzheimer's disease coincides with particular forms of cancer, rheumatoid arthritis, diabetes and Down's syndrome under the denominator 'amyloidosis'. This is a collection of diseases which are characterized by extracellular deposits of normal or mutated proteins. The amyloid deposits in Alzheimer's are ordered in a characteristic three-dimensional pattern of so-called "beta-pleated sheets". The subunit protein component consists of the amyloid beta-protein (A beta-P). This is a small fragment of approximately 40 amino acids which is released by enzymes from the transmembrane beta-amyloid precursor protein (beta-APP). The processing of this precursor protein can take place in a number of ways and then results in a normally occurring soluble fragment or, under certain conditions via alternative proteases, an intact beta-fragment. The production of amyloid beta-protein is therefore in itself a normal physiological event and the existence of A beta-P can be demonstrated in the cerebral fluid (CFS) of healthy humans. However, the deposit of amyloid beta-protein is the primary event causing Alzheimer's disease.

Other proteins are also associated with the amyloid deposits, including SAP and serum amyloid A (SAA). According to the invention it has now been found that both SAP and SAA can bind to LPS and are capable of neutralizing the biological activity of LPS. As such these two amyloid associated plasma proteins have no structural affinity.

According to the present invention it is now proposed that LPS enters into a binding with the serum amyloid proteins SAP and SAA, whereby the role of SAP and SAA in the initiation of amyloid deposits is influenced. It is suspected that through binding of LPS to SAP and SAA the occurrence of deposits is stimulated. The hypothesis now is that (chronic) bacterial infections, and particularly LPS as environmental factor, contribute to the development of Alzheimer's disease. It is in fact suspected that the basis for Alzheimer's is the alternative processing of the beta-amyloid precursor protein, which possibly takes place outside the brain in the circulation. There are indications that soluble amyloid beta-protein in plasma is associated with lipoproteins, in particular the VHDL and HDL3 fractions, in which it is complexed with the apolipo protein J (ApoJ). The ApoJ/amyloid beta-protein complex is capable of passing through the blood-brain barrier. In this manner the amyloid beta-protein enters the brain, where it is deposited. SAA is likewise an apolipo protein which is associated with the HDL fraction and particularly with the HDL3 subfraction.

It is further suspected that LPS also plays a part in the development of Alzheimer's disease via an indirect route. Cytokines, such as interleukin 1 (IL-1) and interleukin 6 (IL-6), lead to over-expression of beta-amyloid precursor protein in the vessel wall and in microglia and astrocytes in the brain. This points to a role for the acute-phase response in the development of Alzheimer's disease. LPS is a potent initiator of the acute-phase response and also initiates the production of IL-1 and IL-6. Because both cytokines result in more beta-amyloid precursor protein, an indirect role of LPS is assumed.

The SAP itself and fragments derived from SAP (peptides) with a strong LPS-binding and neutralizing action can therefore be of importance in eliminating the part played by LPS in the development of Alzheimer's disease.

This influence can relate to the initiation as well as the further progression of the disease.

According to a third aspect the present invention therefore provides the use of SAP and/or SAP fragments thereof for the manufacture of a pharmaceutical composition for the therapeutic and preventive treatment of Alzheimer's disease.

The pharmaceutical compositions, which according to the invention contain SAP and/or one or more SAP fragments (peptides) as active ingredient, will be particularly intended for parenteral, and then particularly intravenous use. The pharmaceutical compositions can be prepared by combining (i.e. mixing dissolving etc.) SAP and/or one or more SAP fragments with pharmaceutically acceptable excipients suitable for intravenous administration. The concentration of the active ingredient in a pharmaceutical composition can vary between 0.001% and 100%, depending on the nature of the treatment and the manner of administration. The dose of the active ingredient to be administered likewise depends on the administering route and application but can for instance vary between 0.01 μg and 1 mg per kg body weight, preferably between 0.1 μg and 100 μg per kg body weight.

In addition to use in a pharmaceutical composition, SAP and/or the SAP fragments can also be used for diagnosis of infection with Gram-negative bacteria or sepsis. For this purpose the invention provides a diagnostic method for demonstrating the presence of endotoxin in blood or blood fractions, such as serum or plasma, comprising of bringing a carrier with SAP and/or endotoxin-binding SAP fragments bound thereto into contact with a blood sample for testing in order to enable binding of endotoxin to SAP(-fragments), removing non-bound material and visualizing and/or quantifying the binding between endotoxin and SAP(-fragments).

The invention further provides a diagnostic kit for performing the method, comprising a carrier having bound thereto SAP and/or endotoxin-binding fragments thereof, and means for visualizing and/or quantifying binding between endotoxin and SAP(-fragments).

The carrier can take different forms, such as a microtitre plate, a column, a membrane or beads. These latter can for instance be magnetic beads, such as Dyna-beads™.

Binding of endotoxin to SAP or SAP fragments can be detected in different ways. Use can thus be made of a labelled antibody against endotoxin.

In the present application the terms 'SAP fragment(s)', 'peptide(s)' and 'endotoxin-binding peptide(s)' are used interchangeably.

The binding of SAP to endotoxin was found by "fishing" in plasma with magnetic beads having endotoxin bound thereto. The neutralizing action was tested on monocytes, neutrophils and in mice. In addition, SAP fragments were manufactured and the neutralizing action thereof was tested on monocytes. Details of these tests are described in the examples following hereinbelow, which are only given by way of illustration and are not intended to limit the invention in any way whatever.

Reference will be made in the examples to the following accompanying figures:

FIG. 1A shows an SDS-PAGE gel of LPS-Beads which are incubated with serum pre-incubated with free LPS.
lane 1: markers (respectively from top to bottom 92, 66, 45, 31 an d21 kDa),
lane 2: without pre-incubation with free LPS,
lane 3: pre-incubation with 100 $\mu$g/ml free LPS
lane 4: pre-incubation with 10 $\mu$g/ml free LPS
lane 5: pre-incubation with 1 $\mu$g/ml free LPS.

FIG. 1B shows an SDS-PAGE gel of LPS-Beads incubation with serum (lane 1, negative control), commercially obtained SAP (lane 2) and markers (lane 3, molecular weight respectively from top to bottom 92, 66, 45, 31 and 21 kDa).

FIG. 2 shows the effect of SAP on LPS-binding to monocytes. Plotted on the X-axis is the concentration of SAP. The Y-axis shows the average fluorescence which represents the ReLPS-binding.

FIG. 3 shows the inhibition of the LPS priming of neutrophils by SAP in the presence and absence of LPS. In the graph the luminescence counts are plotted against the measurement time (in minutes).

FIG. 4 shows the effect of peptides (SAP fragments) according to the invention on the binding of LPS to monocytes. Plotted on the X-axis is the concentration of the peptides. The Y-axis shows the average fluorescence, which represents the ReLPS-binding.

EXAMPLES

Example 1

Identification and isolation of SAP as endotoxin-binding molecule 1.1 Materials and method A 1 mg/ml solution of LPS of Salmonella Re595 (Sigma; L9764) in carbonate buffer (0.1 M, pH 9.5) is incubated for 24 hours with $5\times10^7$ DynaBeads™ (M450, Dynal A. S., Oslo, Norway) activated with Tosyl. The beads loaded with LPS are washed 3x and stored in HBSS+0.1% Na-azide ($5\times10^7$ b/ml). A 10% dilution (1 to 10 dilution) of serum of healthy volunteers is mixed with $5\times10^6$ LPS-Beads for 30 minutes at 22° C. The serum has optionally been incubated before hand with different concentrations of free LPS. The beads are washed 3x with HBSS (Gibco BRL, Gaithersburg, Md., US) and subsequently resuspended in 25 $\mu$l SDS-PAGE sample buffer (with 2% SDS and 2.5% DTT). After boiling for 3 minutes at 100° C. the sample is analyzed on a 12.5% SDS-PAGE (Mini-ProteanII; Bio-Rad). The proteins present are stained with Coomassie Blue. A sample with Marker proteins of known sizes (Bio-Rad) serves as reference. For identification the proteins are transferred after SDS-PAGE to nitrocellulose paper by means of a Mini Trans-Blotter™. The proteins are stained with Coomassie Blue, and the protein around 30 kDa is excited and dissolved in buffer. The sequence of this sample is determined. SAP is isolated from normal human serum by making use of the Ca-dependent binding to Sepharose. With delipidated serum, which is manufactured by centrifuging serum for 4 minutes at 16,000 rpm, two precipitation steps are first performed (successively with $BaCl_2$ and $NH_4SO_4$) followed by anion exchange chromatography on a Mono-Q column (Pharmacia). The eluate at 0.2 to 0.3 M NaCl is finally guided over a Sepharose-4B column and 95% pure SAP is obtained by elution with EDTA (analysis on SDS-PAGE and with a specific ELISA). For the purification method see also Skinner & Cohen, Methods in Enzymology, vol. 163, pages 523–536 (1988).

1.2 Results

1. FIG. 1A shows an example of a SDS-PAGE gel of LPS-beads incubated with serum. For specificity of the reaction the serum was first incubated with different concentrations (100, 10, 1 and 0 $\mu$g/ml) of free ReLPS (L964, Sigma Chemicals, St. Louis, Mo. US) before the mixture was incubated with the LPS-Beads. This demonstrates that when SAP is saturated with free LPS no further binding to the LPS-Beads occurs (lanes 3 and 4). It follows herefrom that SAP is also capable of binding with free LPS.

2. Sequence determination of the first 17 amino acids (N-terminal) of the ±30 kDa protein resulted in a sequence which corresponds 100% with Serum Amyloid P-Component (SAP). The probability that the protein is SAP is hereby 89%. This protein and SAP were used to demonstrate the neutralizing action thereof.

3. Binding of commercially obtained SAP (Calbiochem; 565190) to LPS-Beads by analysis with SDS-PAGE is shown in FIG. 1B. This again also shows that the component from serum which binds to the LPS-Beads is indeed SAP.

Example 2

Inhibition of endotoxin-induced monocyte activation by SAP 2.1 Materials and method LPS of Salmonella Re595 (ReLPS, supra) is labelled with FITC (Sigma; F7250) under conditions in which LPS is present as monomer, resulting in a FITC-LPS preparation with a ratio of 1 molecule FITC per molecule PLS. After extension desalting and dialysis against PBS, the stock solution of FITC-LPS is stored at −20° C. Mononuclear leukocytes (monocytes and lymphocytes) are isolated from heparin blood of healthy volunteers via a Ficol (Pharmacial) gradient in accordance with a standard method. After washing the cells are resuspended in isotonic HEPES buffer (with 1 mM $CaCl_2$ and 2% BSA). Preparations with SAP are mixed with FITC-LPS and subsequently added to $3\times10^5$ mononuclear cells and 30 ng/ml recom- Example 3

Inhibition of endotoxin-induced monocyte activation by SAP fragments 3.1 Materials and method The test was performed in the same manner as described in example 2. However, SAP fragments (peptides) were used instead of SAP. The amino acid composition of the tested peptides is shown in table 2, as well as the concentration at which 50% inhibition occurs. FIG. 4 shows the inhibition at different concentrations. 'PEP 27–39scr' herein represents a peptide with the same amino acid composition as PEP 27–39, but in a different sequence.

3.2 Results Table 2 and FIG. 4 show that particularly PEP 27–39 has a very good activity. PEP 33–38, PEP 32–39, PEP 30–37 and PEP 29–36 also still have an acceptable activity. The result with PEP 27–39 scr shows that not only the amino acid composition but also the amino acid sequence have an influence on the inhibiting action of a peptide on binding of LPS to monocytes.

TABLE 2

| Amino Acid Number | 27 | 28 | 29 | 30 | 31 | 32 | 33 | 34 | 35 | 36 | 37 | 38 | 39 | 50% inhibition concentration | SEQ ID NO |
|---|---|---|---|---|---|---|---|---|---|---|---|---|---|---|---|
| SAP | | | | | | | | | | | | | | 0.05 μM | |
| PEP 29–39 | | | Glu | Lys | Pro | Leu | Gln | Asn | Phe | Thr | Leu | Cys | Phe | Arg | Ala | 0.1 μM | 1 |
| PEP 33–38 | | | | | | | Phe | Thr | Leu | Cys | Phe | Arg | | 3.5 μM | 2 |
| PEP 32–39 | | | | | | Asn | Phe | Thr | Leu | Cys | Phe | Arg | Ala | 2 μM | 3 |
| PEP 33–38 | | | | | Gln | Asn | Phe | Thr | Leu | Cys | Phe | Arg | | >100 μM | 6 |
| PEP 30–37 | | | | Leu | Gln | Asn | Phe | Thr | Leu | Cys | Phe | | | 4.5 μM | 4 |
| PEP 29–36 | | | Pro | Leu | Gln | Asn | Phe | Thr | Leu | Cys | | | | 6.5 μM | 5 |
| PEP 28–35 | | Lys | Pro | Leu | Gln | Asn | Phe | Thr | Leu | | | | | >100 μM | 7 |
| PEP 27–34 | Glu | Lys | Pro | Leu | Gln | Asn | Phe | Thr | | | | | | >106 μM | 8 |

Glu-Glutamate;
Lys-Lysine;
Pro-Proline;
Leu-Leucine;
Gln-Glutamine;
Asn-Asparagine;
Phe-Phenylalanine;
Thr-Threonine;
Cys-Cysteine;
Arg-Arginine;
Ala-Alanine binant LSP (obtained from Dr. Lichtenstein) in a total volume of 50 μl and a FITC-LPS concentration of 2.5 ng/ml. After an incubating period of 30 minutes at 37° C., the samples are stored on ice. Analysis of monocyte-associated FITC-LPS binding takes place with PAC Scan™ Flow cytometer. Forward and Sideward Scatter parameters are used to identify the monocyte population. With LysisII™ software (Beckton & Dickinson) the average fluorescence value of 5000 monocytes is calculated. See also Weersing A. J. L. et al., J. Immunol. 145, 318–324 (1990)).

2.2 Results

1. FIG. 2 shows the concentration-dependent inhibition of FITC-LPS binding to monocytes in vitro. This shows that the more SAP is added in the assay, the less LPS associates itself with the monocytes. Since association of LPS with the monocyte is the first step in the activation of the monocyte, this is a very strong indication that SAP will also inhibit the monocyte activation in vivo at a very early stage.

Example 4

Inhibition of endotoxin-induced neutrophil activation by SAP 4.1 Materials and method Neutrophils are isolated from heparin blood of healthy volunteers via a Histopaque-Picoll gradient in accordance with a standard method (Van Amerafoort, E. S. & J. A. G. van Strijp, Cytometry 17, 294–301 (1994). The remaining erythrocytes in the neutrophil fraction are lysed with sterile water (for 30 seconds) and, after reinstatement of the isotonicity, the fraction is washed. The cells are finally inserted (suspended) in HGSS+2% Human Serum Albumin (HSA). Cells ($1\times10^4$) are incubated with 1 ng/ml ReLPS, 30 ng/ml recombinant LPS-binding protein (r-LPS) and a sample SAP in a total volume of 100 μl for 30 minutes at 37° C. The samples are subsequently placed in a luminometer (Berthold; Autolumat LB953), whereafter via automatic injection luminol (180 μM) and 1 μM fMLP (formylmethyonyl-leucyl-phenylalanine) are added as stimulus to each tube. The luminescence response is measured continuously for 15 minutes and the results expressed as total luminescence response (area under the graph). See also Weersink et al., Immunology 83, 617–623 (1994).

4.2 Results

1. FIG. 3 shows the inhibition of the LPS "priming" of neutrophils by SAP. In the graph the luminescence counts are plotted against the measurement time (in minutes). This shows that the activation of meutrophils by LPS is greatly reduced by SAP. This is a strong indication that the toxicity of LPS can also be reduced in vivo by SAP.

Example 5

Inhibition of endotoxin-induced sepsis in vivo 5.1 Materials and method. In vivo protection experiments are performed in a peritonitis model in the mouse (Cross et al., Infect. and Immunity 61, 2741–2747 (1993)) with ReLPS or intact Gram-negative bacteria. The SAP preparation is incubated beforehand with ReLPS or O18K5 bacteria (Cross et al., supra) and subsequently administered intraperitoneally to BALB/c mice in a $3 \times LD_{50}$ dose. Survival was followed for 7 days.

What is claimed is:

1. A method for treating an animal or patient in need of lipopolysaccharide neutralization, comprising administering in unit dosage form an amount of a peptide, said peptide comprising Serum Amyloid P component or at least one endotoxin-binding fragment thereof, effective to neutralize lipopolysaccharide in an animal or patient thus treated.

2. A method for treating an animal or patient in need of treatment for sepsis, comprising administering in unit dosage form an amount of a peptide, said peptide comprising Serum Amyloid P component or at least one endotoxin-binding fragment thereof, effective to treat sepsis in an animal or patient on which said method is practiced.

3. A method for treating an animal or patient in need of lipopolysaccharide neutralization, comprising administering in unit dosage form an amount of a peptide, said peptide comprising at least a portion of the sequence of amino acids 27–39 (SEQ ID NO:1) of Serum Amyloid P component, effective to neutralize lipopolysaccharide in an animal or patient thus treated.

4. The method according to claim 3 wherein said peptide has a sequence selected from the group consisting of: Glu-Lys-Pro-Leu-Gln-Asn-Phe-Thr-Leu-Cys-Phe-Arg-Ala (SEQ ID NO:1), further designated as PEP 27–39; Phe-Thr-Leu-Cys-Phe-Arg (SEQ ID NO:2), further designated as PEP 33–38; Asn-Phe-Thr-Leu-Cys-Phe-Arg-Ala (SEQ ID NO: 3), further designated as PEP 32–39; Leu-Gln-Asn-Phe-Thr-Leu-Cys-Phe (SEQ ID NO:4), further designated as PEP 30–37; and Pro-Leu-Gln-Asn-Phe-Thr-Leu-Cys (SEQ ID NO:5), further designated as PEP 29–36.

5. A method for treating an animal or patient in need of treatment for sepsis, comprising administering in unit dosage form an amount of a peptide, said peptide comprising at least a portion of the sequence of amino acids 27–39 (SEQ ID NO:1) of Serum Amyloid P component, effective to treat sepsis in an animal or patient on which said method is practiced.

6. The method according to claim 5 wherein said peptide has a sequence selected from the group consisting of Glu-Lys-Prop-Leu-Gln-Asn-Phe-Thr-Leu-Cys-Phe-Arg-Ala (SEQ ID NO:1), further designated as PEP 27–39; Phe-Thr-Leu-Cys-Phe-Arg (SEQ ID NO:2), further designated as PEP 33–38; Asn-Phe-Thr-Leu-Cys-Phe-Arg-Ala (SEQ ID NO: 3), further designated as PEP 32–39; Leu-Gln-Asn-Phe-Thr-Leu-Cys-Phe (SEQ ID NO:4), further designated as PEP 30–37; and Pro-Leu-Gln-Asn-Phe-Thr-Leu-Cys (SEQ ID NO:5), further designated as PEP 29–36.

* * * * *